US007601817B2

(12) United States Patent
Mozier

(10) Patent No.: US 7,601,817 B2
(45) Date of Patent: Oct. 13, 2009

(54) ANTIBODY PEG POSITIONAL ISOMERS, COMPOSITIONS COMPRISING SAME, AND USE THEREOF

(75) Inventor: Ned M. Mozier, St. Charles, MO (US)

(73) Assignee: UCB Pharma S.A., Brussels (BE)

( * ) Notice: Subject to any disclaimer, the term of this patent is extended or adjusted under 35 U.S.C. 154(b) by 387 days.

(21) Appl. No.: 10/515,677

(22) PCT Filed: May 28, 2003

(86) PCT No.: PCT/US03/16619

§ 371 (c)(1),
(2), (4) Date: Dec. 20, 2005

(87) PCT Pub. No.: WO03/099226

PCT Pub. Date: Dec. 4, 2003

(65) Prior Publication Data

US 2006/0110382 A1    May 25, 2006

Related U.S. Application Data

(60) Provisional application No. 60/383,765, filed on May 28, 2002.

(51) Int. Cl.
C07K 16/24 (2006.01)
(52) U.S. Cl. ............... 530/388.1; 424/133.1; 424/180.1
(58) Field of Classification Search ...................... None
See application file for complete search history.

(56) References Cited

U.S. PATENT DOCUMENTS

| 5,643,575 | A | 7/1997 | Martinez et al. |
| 5,919,452 | A | 7/1999 | Le et al. |
| 5,919,455 | A | 7/1999 | Greenwald et al. |
| 5,932,462 | A | 8/1999 | Harris et al. |
| 6,113,906 | A | 9/2000 | Greenwald et al. |

FOREIGN PATENT DOCUMENTS

| EP | 0 239 400 A2 | 9/1987 |
| EP | 0 392 745 A2 | 10/1990 |
| GB | 2 246 570 A | 2/1992 |
| GB | 2 297 145 A | 7/1996 |
| WO | WO 86/01533 | 3/1986 |
| WO | WO 89/01476 | 2/1989 |
| WO | WO 90/00195 | 1/1990 |
| WO | WO 90/07861 | 7/1990 |
| WO | WO 91/09967 | 7/1991 |
| WO | WO 92/11383 | 7/1992 |
| WO | WO 92/22583 | 12/1992 |
| WO | WO 93/06231 | 4/1993 |
| WO | WO 98/20734 | 5/1998 |
| WO | WO 98/25971 | 6/1998 |
| WO | WO 01/04585 | 1/2001 |
| WO | WO 01/94585 | 12/2001 |

OTHER PUBLICATIONS

Monkarsh et al. Anal. Biochem. vol. 247, p. 434-440, 1997.*
Adorini, L. and Sinigaglia, F., "Pathogenesis and immunotherapy of autoimmune diseases," *Trends in Immunology Today*, 18(5):209-211, (1997).
Bodmer, M. et al., "Preclinical review of anti-tumor necrosis factor monoclonal antibodies," *Critical Care Medicine*, 21(10):S441-S446, (1993).
Crameri, A., et al., "DNA shuffling of a family of genes from diverse species accelerates directed evolution," *Nature*, 391(6664):288-291, (Jan. 1988).
Feldman, M., et al., "Anti-TNFα Therapy Is Useful in rheumatoid Arthritis and Crohn's Disease: Analysis of the Mechanism of Action Predicts Utility in Other Diseases," *Transplantation Proceedings*, 30:4126-4127. (1998).
Feldmann, M., et al., "Anti-Tumor Necrosis Factor-α Therapy of Rheumatoid Arthritis," *Advances in Immunology*, 64:283-350, (1997).
Fendly, B.M., et al., "Murine Monoclonal Antibodies Defining Neutralizing Epitopes on Tumor Necrosis Factor," *Hybridoma*, 6(4):359-370. (1987).
Flanagan, J.G. and Rabbitts, T.H., "Arrangement of human immunoglobulin heavy chain constant region genes implies evolutionary duplication of a segment containing γ, ϵ and α genes," *Nature*, 300(5894):709-713, (Dec. 1982).
Genebank Accession No. J00241, version J00241.1 GI:185938, "Human Ig germline kappa-L chain, C region (inv3 allele)," accessed by PTO on Apr. 6, 2002, (Jan. 5, 1995).
Hieter, P.A., et al., "Cloned Human and Mouse Kappa Immunoglobulin Constant and J Region Genes Conserve Homology in Functional Segments," *Cell*, 22(Part 1):197-207, (Nov. 1980).
Keffer, J., et al., "Transgenic mice expressing human tumour necrosis factor: a predictive genetic model of arthritis," *The EMBO Journal*, 10(13):4025-4031, (1991).
Kirschenbaum, L., et al., "Antibodies to TNF-α: Too little, too late?," *Critical Care Medicine*, 26(10):1625-1626, (1998).
Low, N.M., et al., "Mimicking Somatic Hypermutation: Affinity Maturation of Antibodies Displayed on Bacteriophage Using a Bacterial Mutator Strain," *J. Mol. Biol.*, 260:359-368, (1996).
Marks, J.D., et al.. "By-Passing Immunization: Building High Affinity Human Antibodies By Chain Shuffling," *Bio/Technology*, 10:779-783, (Jul. 1992).

(Continued)

*Primary Examiner*—Michael Szperka
*Assistant Examiner*—Yunsoo Kim
(74) *Attorney, Agent, or Firm*—Cozen O'Connor

(57) ABSTRACT

The present invention relates to recombinant protein PEG positional isomers. More specifically, it relates to PEG positional isomers of an antibody having specificity for antigenic determinants of human tumor necrosis factor alpha (TNFα). More specifically, it relates to PEG positional isomers of CDP870. The present invention also relates to compositions comprising the PEG positional isomers and therapeutic uses of the composition for treating a disease medicated by TNFα including acute and chronic immune and immunoregulatory disorders and rheumatoid-or osteo-arthritis.

4 Claims, 2 Drawing Sheets

OTHER PUBLICATIONS

Meager, A., et al., "Preparation and Characterization of Monoclonal Antibodies Directed Against Antigenic Determinants of Recombinant Human Tumour Necrosis Factor (rTNF)." *Hybridoma*, 6(3):305-311, (1987).

McKown, K.M., et al., "Lack of Efficacy of Oral Bovine Type II Collagen Added to Existing Therapy in Rheumatoid Arthritis," *Arthritis and Rheumatism*, 42(6):1204-1208, (Jun. 1999).

Patten, P.A., et al., "Applications of DNA shuffling to pharmaceuticals and vaccines," *Current Opinion in Biotechnology*, 87:724-733, (1997).

Rankin, E.C.C., et al., "The Therapeutic Effects of an Engineered Human Anti-Tumour Necrosis Factor Alpha Antibody (CDP571) in Rheumatoid Arthritis," *British Journal of Rheumatology*, 34:334-342, (1995).

Riechmann, L., et al., "Reshaping human antibodies for therapy," *Nature*, 332:323-327, (Mar. 1988).

Russell, W.K. et al., "Proteolysis in Mixed Organic-Aqueous Solvent Systems: Applications for Peptide Mass Mapping Using Mass Spectrometry," *Anal. Chem.*, 73:2682-2685, (2001).

Shimamoto, Y., et al., "Monoclonal antibodies against human recombinant tumor necrosis factor: prevention of endotoxic shock," *Immunology Letters*, 17:311-318, (1988).

Stephens, S., et al., "Comprehensive pharmacokinetics of a humanized antibody and analysis of residual anti-idiotypic responses," *Immunology*, 85:668-674, (1995).

Thompson, J., et al., "Affinity Maturation of a High-affinity Human Monoclonal Antibody Against the Third Hypervariable Loop of Human Immunodeficiency Virus: Use of Phage Display to Improve Affinity and Broaden Strain Reactivity," *J. Mol. Biol.*, 256:77-88. (1996).

Tracey, K.J., et al., "Shock and Tissue Injury Induced by Recombinant Human Cachectin," *Science*, 234:470-474, (1985).

Vaughan, T., et al., "Human antibodies by design," *Nature Biotechnology*, 16:535-539, (Jun. 1998).

Verhoeyen, M., et al., "Reshaping Human Antibodies: Grafting an Antilysozyme Activity," *Science*, 239:1534-1536, (Mar. 25, 1988).

Wherry, J.C., "Tumor necrosis factor and the therapeutic potential of anti-tumor necrosis factor antibodies," *Critical Care Medicine*, 21(10):S436-S440, (Oct. 1993).

Williams, R.O., et al., "Anti-tumor necrosis factor ameliorates joint disease in murine collagen-induced arthritis," *Proc. Natl. Acad. Sci. USA*, 89:9784-9788, (Oct. 1992).

Wu, T.T. and Kabat, E.A., "An Analysis of the Sequences of the Variable Regions of Bence Jones Proteins and Myeloma Light Chains and Their Implications for Antibody Complementarity," *J. Exp. Med.*, 132:211-250, (1970).

Yang, W.P., et al., "CDR Walking Mutagenesis for the Affinity Maturation of a Potent Human Anti-HIV-1 Antibody into the Picomolar Range," *J. Mol. Biol.*, 254:392-403. (1995).

PCT International Search Report dated May 25, 2004 for International Application No. PCT/US03/16619, International Filing Date: May 28, 2003.

M. Aslam and A. Dent, "Bioconjugation Protein Coupling Techniques for the Biomedical Sciences," Grove Publishers, New York (1998).

J. Milton Harris (ed.), "Poly(ethyleneglycol) Chemistry, Biotechnical and Biomedical Applications," Plenum Press, New York (1992).

J. Milton Harris and S. Zalipsky (eds.), "Poly(ethyleneglycol) Chemistry and Biological Applications," American Chemical Society, Washington, D.C. (1997).

Kabat, et al., "In Sequences of Proteins of Immunological Interest," U.S. Department of Health and Human Services, NIH, USA, (1987).

Remington's Pharmaceutical Sciences, Mack Publishing Company, New Jersey (1991).

* cited by examiner

FIG 1

*Light Chain*

DIQMTQSPSS LSASVGDRVT ITCKASQNVG TNVAWYQQKP GKAPKALIYS

ASFLYSGVPY RFSGSGSGTD FTLTISSLQP EDFATYYCQQ YNNYPLTFGQ

GTKVEIKRTV AAPSVFIFPP SDEQLKSGTA SVVCLLNNFY PREAKVQWKV

DNALQSGNSQ ESVTEQDSKD STYSLSSTLT LSKADYEKHK VYACEVTHQG

LSSPVTKSFNRGEC    SEQ ID NO:1

*Heavy Chain*

EVQLVESGGG LVQPGGSLRL SCAASGYVFT DYGMNWVRQA PGKGLEWMGW

INTYIGEPIY ADSVKGRFTF SLDTSKSTAY LQMNSLRAED TAVYYCARGY

RSYAMDYWGQ GTLVTVSSAS TKGPSVFPLA PSSKSTSGGT AALGCLVKDY

FPEPVTVSWN SGALTSGVHT FPAVLQSSGL YSLSSVVTVP SSSLGTQTYIC

NVNHKPSNT KVDKKVEPKS CDKTHTCAA    SEQ ID NO:2
                          |
                         PEG

FIG 2

Light Chain:

DIQMTQSPSSLSASVGDR VTITCKASQNVGTNVAWYQQKPGKAPKALIY

SASFLYSGVPYRFSGSGSGTDFTLTISSLQPEDFATYYCQQYNIYPLTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC    SEQ ID NO:1
            214
             |
           PEG

Heavy Chain:

EVQLVESGGGLVQPGGSLRLSCAASGYVFTDYGMNWVRQAPGGLEWMGWI

NTYIGEPIYADSVKGRFTFSLDTSKSTAYLQMNSLRAEDTAVYYCARGYR

SYAMDYWGQGTLVTVSSASTKGPSVFPLAPSSKSTSGGTAALGCLVKDYF

PEPVTVSWNSGALTSGVHTFPAVLQSSGLYSLSSVVTVPSSSLGTQTYIC
                221     227

NVNHKPSNTKVDKKVEPKSCDKTHTCAA    SEQ ID NO:2

ANTIBODY PEG POSITIONAL ISOMERS, COMPOSITIONS COMPRISING SAME, AND USE THEREOF

CROSS-REFERENCE TO RELATED APPLICATIONS

The present application is a 35 U.S.C. 371 National Stage Application of International Application No. PCT/US03/16619, International Filing Date: May 28, 2003, which claims priority to International Application No. PCT/US03/08608, International Filing Date: Mar. 20, 2003, which claims benefit of priority to U.S. Provisional Patent Application Ser. No. 60/383,765, filed May 28, 2002, all of which are incorporated herein by reference in their entirety.

FIELD OF THE INVENTION

The present invention relates to recombinant protein PEG positional isomers. More specifically, it relates to PEG positional isomers of an antibody having specificity for antigenic determinants of human tumor necrosis factor alpha (TNFα). More specifically, it relates to PEG positional isomers of CDP870. The present invention also relates to compositions comprising the PEG positional isomers and therapeutic uses of the antibody.

BACKGROUND OF THE INVENTION

In an antibody molecule, there are two heavy chains and two light chains. Each heavy chain and each light chain has at its N-terminal end a variable domain. Each variable domain is composed of four framework regions (FRs) alternating with three complementarily determining regions (CDRs). The residues in the variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or CDR, of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-335 (CDRHI), residues 50-65 (CDRH2) and residues 95-102 (CDRH3) according to the Kabat numbering.

The CDRs of the light chain variable domain are located at residues 24-34 (CDRL1), residues 50-56 (CDRL2) and residues 89-97 (CDRL3) according to the Kabat numbering.

Construction of CDR-grafted antibodies is described in European Patent Application EP-A-0239400, which discloses a process in which the CDRs of a mouse monoclonal antibody are grafted onto the framework regions of the variable domains of a. human immunoglobulin by site directed mutagenesis using long. oligonucleotides. The CDRs determine the antigen binding specificity of antibodies and are relatively short peptide sequences carried on the framework regions of the variable domains.

The earliest work on humanising monoclonal antibodies by CDR-grafting was carried out on monoclonal antibodies recognising synthetic antigens, such as NP. However, examples in which a mouse monoclonal antibody recognising lysozyme and a rat monoclonal antibody recognising an antigen on human T-cells were humanised by CDR-grafting have been described by Verhoeyen et al. (*Science*, 239, 1534-1536, 1988) and Riechmann et al. (*Nature*, 332, 323-324, 1988), respectively.

Riechmann et al., found that the transfer of the CDRs alone (as defined by Kabat (Kabat et al. (supra) and Wu et al., *J. Exp. Med.*, 132, 211-250, 1970)) was not sufficient to provide satisfactory antigen binding activity in the CDR-grafted product. It was found that a number of framework residues have to be altered so that they correspond to those of the donor framework region. Proposed criteria for selecting which framework residues need to be altered are described in International Patent Application WO 90/07861.

A number of reviews discussing CDR-grafted antibodies have been published, including Vaughan et al. (*Nature Biotechnology*, 16, 535-539, 1998).

TNFα is a pro-inflammatory cytokine that is released by and interacts with cells of the immune system. Thus, TNFα is released by macrophages that have been activated by lipopolysaccharides (LPS) of gram negative bacteria. As such, TNFα appears to be an endogenous mediator of central importance involved in the development and pathogenesis of endotoxic shock associated with bacterial sepsis. TNFα has also been shown to be up-regulated in a number of human diseases, including chronic diseases such as rheumatoid arthritis, Crohn's disease, ulcerative colitis, and multiple sclerosis. Mice transgenic for human TNFα produce high levels of TNFα constitutively and develop a spontaneous, destructive polyarthritis resembling rheumatoid arthritis (Kaffer et al., *EMBO J.*, 10, 4025 4031, 1991). TNFα is therefore referred to as a pro-inflammatory cytokine.

Monoclonal antibodies against TNFα have been described in the prior art. Meager et al., (*Hybridoma*, 6, 305-311, 1987) describe murine monoclonal antibodies against recombinant TNFα. Fendly et al., (*Hybridoma*, 6, 359-370, 1987) describe the use of murine monoclonal antibodies against recombinant TNFα in defining neutralising epitopes on TNF. Shimamoto et al., (*Immunology Letters*, 17, 311-318, 1988) describe the use of murine monoclonal antibodies against TNF7 and their use in preventing endotoxic shock in mice. Furthermore, in International Patent Application WO 92/11383, recombinant antibodies, including CDR-grafted antibodies, specific for TNFα are disclosed. Rankin et al., (*British J. Rheumatology*, 34, 334-342, 1995) describe the use of such CDR-grafted antibodies in the treatment of rheumatoid arthritis. U.S. Pat. No. 5,919,452 discloses anti-TNF chimeric antibodies and their use in treating pathologies associated with the presence of 5 TNF.

Antibodies to TNFα have been proposed for the prophylaxis and treatment of endotoxic shock (Beutler et al., *Science*, 234, 470-474, 1985). Bodmer et al., (*Critical Care Medicine*, 21, S441-S446, 1993) and Wherry et al., (*Critical Care Medicine*, 21, S436S440, 1993) discuss the therapeutic potential of anti-TNFα antibodies in the treatment of septic shock. The use of anti-TNFα antibodies in the treatment of septic shock is also discussed by Kirschenbaum et al., (*Critical Care Medicine*, 26, 1625-1626, 1998). Collagen-induced arthritis can be treated effectively using an anti-TNFα monoclonal antibody (Williams et al. (*PNAS-USA*, 89, 9784-9788, 1992)).

Increased levels of TNFα are found in both the synovial fluid and peripheral blood of patients suffering from rheumatoid arthritis. When TNFα blocking agents are administered to patients suffering from rheumatoid arthritis, they reduce inflammation, improve symptoms, and retard joint damage (McKown et al. (*Arthritis Rheum*., 42, 1204-1208, 1999).

The use of anti-TNFα antibodies in the treatment of rheumatoid arthritis and 20 Crohn's disease is discussed in Feldman et al., (*Transplantation Proceedings*, 30, 41264127, 1998), Adorini et al., (*Trends in Immunology Today*, 18, 209-211, 1997) and in Feldman et al., (*Advances in Immunology*, 64, 283-350, 1997). The antibodies to TNFα used in such treatments are generally chimeric antibodies, such as those described in U.S. Pat. No. 5,919,452.

Two TNFα blocking products are currently licensed for the treatment of rheumatoid arthritis. The first, called etanercept, is marketed by Immunex Corporation as Enbrel™. It is a recombinant fusion protein comprising two p75 soluble TNF-receptor domains linked to the Fc portion of a human immunoglobulin. The second, called infliximab, is marketed by Centocor Corporation as Remicade™. It is a chimeric antibody having murine anti-TNFα variable domains and human IgGI constant domains.

The prior art recombinant anti-TNFα antibody molecules generally have a reduced affinity for TNFα compared to the antibodies from which the variable regions or CDRs are derived, generally have to be produced in mammalian cells and are expensive to manufacture. Prior art anti-TNFα, antibodies are described in Stephens et al., (*Immunology*, 85, 668-674, 1995), GB-A-2 246 570 and GB-A-2 297 145.

WO 01/94585 describes antibody molecules having high affinity for TNFα and low immunogenicity in humans, which can be used repeatedly and produced easily and efficiently, to treat chronic inflammatory diseases.

SUMMARY OF THE INVENTION

This invention comprises recombinant protein PEG positional isomers, preferably, PEG positional isomers of an antibody having specificity for antigenic determinants of human tumour necrosis factor alpha (TNFα). The present invention also relates to compositions comprising the isomers and therapeutic uses of the antibody.

BRIEF DESCRIPTION OF THE DRAWINGS

FIG. 1 shows the amino acid sequence of the light and heavy chains of CDP870, the intramolecular disulfide pairing, the predominant intermolecular disulfide pairing between the light and heavy chains and the cysteine for PEG conjugation.

FIG. 2 shows the amino acid sequence of the light and heavy chains of the CDP870 PEG positional isomer where the PEG is attached at Cys 214 of the light chain (CDP870-PEG-1214). The residues of interest (light chain cys-214, heavy chain cys-221 and heavy chain cys-227 are highlighted.

DETAILED DESCRIPTION OF THE INVENTION

In a first aspect, the present invention provides recombinant protein PEG positional isomers, having an alternate PEG attachment site. An "antibody PEG positional isomer" is defined as an antibody having a PEG attachment site other than the predominant PEG attachment site. Preferably, the PEG positional isomer is of an antibody having specificity for antigenic determinants of human tumor necrosis factor alpha (TNFα). Preferably, the TNFα antibody is a TNFα antibody disclosed in WO 01/94585. Preferably, the antibody is CDP870.

WO 01/94585 provides an antibody molecule having specificity for TNFα, comprising a heavy chain wherein the variable domain comprises a CDR (as defined by Kabat et al. (supra)) having the sequence given as H1 in FIG. 3 of WO 01/94585 (SEQ ID NO: 1 of WO 01/94585) for CDRH1, as H2' in FIG. 3 of WO 01/94585 (SEQ ID NO: 2 of WO 01/94585) or as H2 in FIG. 3 of WO 01/94585 (SEQ ID NO: 7 of WO 01/94585) for CDRH2 or as H3 in FIG. 3 of WO 01/94585 (SEQ ID NO: 3 of WO 01/94585) for CDRH3.

The antibody molecule of WO 01/94585 comprises at least one CDR selected from H1, H2' or H2 and H3 (SEQ ID NO: 1; SEQ ID NO: 2 or SEQ ID NO: 7 and SEQ ID NO: 3 of WO 01/94585) for the heavy chain variable domain. Preferably, the antibody molecule comprises at least two and more preferably all three CDRs in the heavy chain variable domain.

In WO 01/94585, there is provided an antibody molecule having specificity for human TNFα, comprising a light chain wherein the variable domain comprises a CDR (as defined by Kabat et al. (supra)) having the sequence given as L1 in FIG. 3 of WO 01/94585 (SEQ ID NO: 4 of WO 01/94585) for CDRL1, L2 in FIG. 3 of WO 01/94585 (SEQ ID NO: 5 of WO 01/94585) for CDRL2 or L3 in FIG. 3 of WO 01/94585 (SEQ ID NO: 6 of WO 01/94585) for CDRL3.

The antibody molecule of WO 01/94585 comprises at least one CDR selected from L1, L2, and L3 (SEQ ID NO: 4 to SEQ ID NO: 6 of WO 01/94585) for the light chain variable domain. Preferably, the antibody molecule comprises at least two and more preferably all three CDRs in the light chain variable domain.

The antibody molecules of WO 01/94585 preferably have a complementary light chain or a complementary heavy chain, respectively.

Preferably, the antibody molecule of WO 01/94585 comprises a heavy chain wherein the variable domain comprises a CDR (as defined by Kabat et al. (supra)) having the sequence given as H1 in FIG. 3 of WO 01/94585 (SEQ ID NO: 1 of WO 01/94585) for CDRH1, as H2' or H2 in FIG. 3 of WO 01/94585 (SEQ ID NO: 2 or SEQ ID NO: 7 of WO 01/94585) for CDRH2 or as H3 in FIG. 3 of WO 01/94585 (SEQ ID NO: 3 of WO 01/94585) for CDRH3 and a light chain wherein the variable domain comprises a CDR (as defined by Kabat et al. (supra)) having the sequence given as L1 in FIG. 3 of WO 01/94585 (SEQ ID NO: 4 of WO 01/94585) for CDRL1, as L2 in FIG. 3 of WO 01/94585 (SEQ ID NO: 5 of WO 01/94585) for CDRL2 or as L3 in FIG. 3 of WO 01/94585 (SEQ ID NO: 6 of WO 01/94585) for CDRL3.

The CDRs given in SEQ IDS NOS: 1 and 3 to 7 of WO 01/94585 and in FIG. 3 of WO 01/94585 are derived from a mouse monoclonal antibody hTNF40. However, SEQ ID NO: 2 of WO 01/94585 consists of a hybrid CDR. The hybrid CDR comprises part of heavy chain CDR2 from mouse monoclonal antibody hTNF40 (SEQ ID NO: 7 of WO 01/94585 and part of heavy chain CDR2 from a human group 3 germline V region sequence.

The complete sequences of the variable domains of the mouse hTNF40 antibody are shown in FIG. 6 of WO 01/94585 (light chain) (SEQ ID NO: 99 of WO 01/94585) and FIG. 7 of WO 01/94585 (heavy chain) (SEQ ID NO: 100 of WO 01/94585). This mouse antibody is referred to below as "the donor antibody".

A first alternatively embodiment of WO 01/94585 is the mouse monoclonal antibody hTNF40 having the light and heavy chain variable domain sequences shown in FIG. 6 of WO 01/94585) (SEQ ID NO: 99 of WO 01/94585) and FIG. 7 of WO 01/94585 (SEQ ID NO: 100 of WO 01/94585), respectively. The light chain constant region of hTNF40 is kappa and the heavy chain constant region is IgG2a.

In a second alternatively embodiment of WO 01/94585, the antibody according to either of the first and second aspects of WO 01/94585 is a chimeric mouse/human antibody molecule, referred to herein as the chimeric hTNF40 antibody molecule. The chimeric antibody molecule comprises the variable domains of the mouse monoclonal antibody hTNF40 (SEQ ID NOS: 99 and 100 of WO 01/94585) and human constant domains. Preferably, the chimeric hTNF40 antibody molecule comprises the human C kappa domain (Hieter et al., *Cell*, 22, 197-207, 1980; Genebank accession number J00241) in the light chain and the human gamma 4 domains (Flanagan et al., *Nature*, 300, 709-713, 1982) in the heavy chain.

In a third alternatively embodiment of WO 01/94585, the antibody is a CDR-grafted antibody molecule. The term "a CDR-grafted antibody molecule" as used herein refers to an antibody molecule wherein the heavy and/or light chain contains one or more CDRs (including, if desired, a hybrid CDR) from the donor antibody (e.g. a murine monoclonal antibody) grafted into a heavy and/or light chain variable region framework of an acceptor antibody (e.g. human antibody).

Preferably, such a CDR-grafted antibody has a variable domain comprising human acceptor framework regions as well as one or more of the donor CDRs referred to above.

When the CDRs are grafted, any appropriate acceptor variable region framework sequence may be used having regard to the class/type of the donor antibody from which the CDRs are derived, including mouse, primate and human framework regions. Examples of human frameworks of WO 01/94585 are KOL, NEWM, REI, EU, TUR, TEI, LAY, and POM (Kabat et al. (supra)). For example, KOL and NEWM can be used for the heavy chain, REI can be used for the light chain and EU, LAY and POM can be used for both the heavy chain and the light chain. The preferred framework regions for the light chain are the human group 1 framework regions shown in FIG. 1 (SEQ ID NOS: 83, 85, 87 and 89 of WO 01/94585). The preferred framework regions for the heavy chain are the human group 1 and group 3 framework regions shown in FIG. 2 (SEQ ID NOS: 91, 93, 95 and 97 and SEQ ID NOS: 106, 107, 108 and 109 of WO 01/94585), respectively.

In a CDR-grafted antibody of WO 01/94585, it is preferred to use as the acceptor antibody one having chains which are homologous to the chains of the donor antibody. The acceptor heavy and light chains do not necessarily need to be derived from the same antibody and may, if desired, comprise composite chains having framework regions derived from different chains.

Also, in a CDR-grafted antibody of WO 01/94585, the framework regions need not have exactly the same sequence as those of the acceptor antibody. For instance, unusual residues may be changed to more frequently occurring residues for that acceptor chain class or type. Alternatively, selected residues in the acceptor framework regions may be changed so that they correspond to the residue found, at the same position in the donor antibody. Such changes should be kept to the minimum necessary to recover the affinity of the donor antibody. A protocol for selecting residues in the acceptor framework regions which may need to be changed is set forth in WO 91/09967.

Preferably, in a CDR-grafted antibody molecule of the WO 01/94585, if the acceptor heavy chain has human group 1 framework regions (shown in FIG. 2 of WO 01/94585) (SEQ ID NOS: 91, 93 95 and 97 of WO 0 1/94585), then the acceptor framework regions of the heavy chain comprise, in addition to one or more donor CDRs, donor residues at positions 28, 69 and 71 according to Kabat et al. (supra)).

Alternatively, if the acceptor heavy chain has group 1 framework regions, then the acceptor framework regions of the heavy chain comprise, in addition to one or more donor CDRs, donor residues at positions 28, 38, 46, 67, 69, and 71 (according to Kabat et al. (supra).

Preferably, in a CDR-grafted antibody molecule of the WO 01/94585, if the acceptor heavy chain has human group 3 framework regions (shown in FIG. 2 of WO 01/94585) (SEQ ID NOS: 106, 107, 108 and 109 of WO 01/94585), then the acceptor framework regions of the heavy chain comprise, in addition to one or more donor CDRs, donor residues at positions 27, 28, 30, 48, 49, 69, 71, 73, 76 and 78 (according to Kabat et al. (supra)).

Preferably, in a CDR-grafted antibody molecule of the WO 01/94585, if the acceptor light chain has human group 1 framework regions (shown in FIG. 1 of WO 01/94585) (SEQ ID NOS: 83, 85, 87 and 89 of WO 01/94585), then the acceptor framework regions of the light chain comprise donor residues at positions 46 and 60 (according to Kabat et al. (supra)).

Donor residues are residues from the donor antibody, i.e. the antibody from which the CDRs were originally derived.

The antibody molecule of WO 01/94585 may comprise: a complete antibody molecule, having full length heavy and light chains; a fragment thereof, such as a Fab, modified Fab, Fab', F(ab')$_2$ or Fv fragment; a light chain or heavy chain monomer or dimer; a single chain antibody, e.g. a single chain Fv in which the heavy and light chain variable domains are joined by a peptide linker. Similarly, the heavy and light chain variable regions may be combined with other antibody domains as appropriate.

Preferably, the antibody molecule of WO 01/94585 is a Fab fragment. Preferably, the Fab fragment has a heavy chain having the sequence given as SEQ ID NO: 111 of WO 01/94585 and light chain having the sequence given as SEQ ID NO: 113 of WO 01/94585. The amino acid sequences given in SEQ ID NO: 111 and SEQ ID NO: 113 of WO 01/94585 are preferably encoded by the nucleotide sequences given in SEQ ID NO: 110 and SEQ ID NO: 112 of WO 01/94585, respectively.

Alternatively, it is preferred that the antibody molecule of WO 01/94585 is a modified Fab fragment wherein the modification is the addition to the C-terminal end of its heavy chain one or more amino acids to allow the attachment of an effector or reporter molecule. The additional amino acids form a modified hinge region containing one or two cysteine residue to which the effector or reporter molecule may be attached. Such a modified Fab fragment preferably has a heavy chain having the sequence given as SEQ ID NO: 115 of WO 01/94585 and the light chain having the sequence given as SEQ ID NO: 113 of WO 01/94585. The amino acid sequence given in SEQ ID NO: 115 of WO 01/94585 is preferably encoded by the nucleotide sequence given in SEQ ID NO: 114 of WO 01/94585.

A preferred effector group of WO 01/94585 is a polymer molecule, which may be attached to the modified Fab fragment to increase its half-life in vivo.

The polymer molecule may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Particular optional substituents, which may be present on the above-mentioned synthetic polymers, include one or more hydroxy, methyl or methoxy groups. Particular examples of synthetic polymers include optionally substituted straight or branched chain poly(ethyleneglycol), poly (propylene glycol) poly(vinylalcohol) or derivatives thereof, especially optionally substituted poly(ethyleneglycol) such as methoxypoly(ethyleneglycol) or derivatives thereof. Particular naturally occurring polymers include lactose, amylose, dextran, glycogen or derivatives thereof. "Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, preferably from 5000 to 40000 Da and more preferably from 25000 to 40000 Da. The polymer size may in particular be selected on the basis of the intended use of the product. Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 25000 Da to 40000 Da.

Particularly preferred polymers include a polyalkylene polymer, such as a poly(ethyleneglycol) or, especially, a methoxypoly(ethyleneglycol) or a derivative thereof, and especially with a molecular weight in the range from about 25000 Da to about 40000 Da.

Each polymer molecule attached to the modified antibody fragment may be covalently linked to the sulphur atom of a cysteine residue located in the fragment The covalent linkage will generally be a disulphide bond or, in particular, a sulphur-carbon bond.

Where desired, the antibody fragment may have one or more effector or reporter molecules attached to it. The effector or reporter molecules may be attached to the antibody fragment through any available amino acid side-chain or terminal amino acid functional group located in the fragment, for example any free amino, imino, hydroxyl or 5 carboxyl group.

An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone, or a disulphide. Such starting materials may be obtained commercially (for example from Shearwater Polymers Inc., Huntsville, Ala., USA) or may be prepared from commercially available starting materials using conventional chemical procedures.

As regards attaching poly(ethyleneglycol) (PEG) moieties, reference is made to "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York.

Where it is desired to obtain an antibody fragment linked to an effector or reporter molecule, this may be prepared by standard chemical or recombinant DNA procedures in which the antibody fragment is linked either directly or via a coupling agent to the effector or reporter molecule either before or after reaction with the activated polymer as appropriate. Particular chemical procedures include, for example, those described in WO 93/62331, WO 92/22583, WO 90/00195 and WO 89/01476. Alternatively, where the effector or reporter molecule is a protein or polypeptide the linkage may be achieved using recombinant DNA procedures, for example as described in WO 86/01533 and EP-A 392 745.

Preferably, the modified Fab fragment of WO 01/94585 is PEGylated (i.e. has PEG (poly(ethyleneglycol)) covalently attached thereto) according to the method disclosed in EP-A 948 544. Preferably, the antibody molecule of WO 01/94585 is a PEGylated modified Fab fragment as shown in FIG. 13 of WO 01/94585. As shown in FIG. 13 of WO 01/94585, the modified Fab fragment has a maleimide group covalently linked to a single thiol group in a modified hinge region. A lysine residue is covalently linked to the maleimide group. To each of the amine groups on the lysine residue is attached a methoxypoly(ethyleneglycol) polymer having a molecular weight of approximately 20,000 Da. The total molecular weight of the entire effector molecule is therefore approximately 40,000 Da. These lysine linked PEGs are referred to as "branched PEG" or "U-PEG" as disclosed in U.S. Pat. Nos. 6,113,906; 5,919,455; 5,643,575; and 5,932,462.

Preferably, in the compound shown in FIG. 13 of WO 01/94585, the heavy chain of the antibody part has the sequence given as SEQ ID NO: 115 of WO 01/94585 and the light chain has the sequence given in SEQ ID NO: 113 OF WO 01/94585. This compound is referred to in WO 01/94585 is CDP870.

The constant region domains of the antibody molecule of WO 01/94585, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required, e.g. for simply blocking TNFα activity.

Also, the antibody molecule of WO 01/94585 may have an effector or a reporter molecule attached to it. For instance, it may have a macrocycle, for chelating a heavy metal atom, or a toxin, such as ricin, attached to it by a covalent bridging structure. Alternatively, procedures of recombinant DNA technology may be used to produce an antibody molecule in which the Fv fragment (CH2, CH3 and hinge domains), the CH2 and CH3 domains or the CH3 domain of a complete immunoglobulin molecule has (have) been replaced by, or has attached thereto by peptide linkage, a functional non-immunoglobulin protein, such as an enzyme or toxin molecule.

The antibody molecule of WO 01/94585 preferably has a binding affinity of at least $0.85 \times 10^{-10}$ M, more preferably at least $0.75 \times 10^{-10}$ M and most preferably at least $0.5 \times 10^{-10}$ M. (It is worth noting that the preferred humanised antibody molecule of WO 01/94585, as described below, has an affinity of about $0.5 \times 10^{-10}$ M, which is better than the affinity of the murine monoclonal antibody from which it is derived. The murine antibody has an affinity of about $0.85 \times 10^{-10}$ M.

Preferably, the antibody molecule of WO 01/94585 comprises the light chain variable domain hTNF40-gL1 (SEQ ID NO: 8 of WO 01/94585) and the heavy chain variable domain gh3hTNF40.4 (SEQ ID NO: 11 of WO 01/94585). The sequences of the variable domains of these light and heavy chains are shown in FIGS. 8 and 11 of WO 01/94585, respectively.

WO 01/94585 also relates to variants of the antibody molecule, which have an improved affinity for TNFα Such variants can be obtained by a number of affinity maturation protocols including mutating the CDRs (Yang et al., *J. Mol. Biol.*, 254, 392-403, 1995), chain shuffling (Marks et al., *Bio/Technology* 10, 779-783, 1992), use of mutator strains of *E. coli* (Low et al., *J. Mol. Biol.*, 250, 359-368, 1996), DNA shuffling (Patten et al., *Curr. Opin. Biotechnol.*, 8, 724-733, 1997), phage display (Thompson et al., *J. Mol. Biol.*, 256, 77-78, 1996) and sexual PCR (Crameri et al., *Nature*, 391, 288-291, 1988). Vaughan et al. (supra) discusses these methods of affinity maturation.

WO 01/94585 also provides a DNA sequence encoding the heavy and/or light chain(s) of the antibody molecule.

WO 01/94585 also relates to a cloning or expression vector comprising one or more DNA sequences. Preferably, the cloning or expression vector comprises two DNA sequences, encoding the light chain and the heavy chain of the antibody molecule.

WO 01/94585 also relates to host cell/vector systems used for expression of the DNA sequences encoding the antibody molecule. Bacterial, for example *E. coli*, and other microbial systems may be used, in part, for expression of antibody fragments such as Fab and F(ab')$_2$ fragments, and especially Fv fragments and single chain antibody fragments, for example, single chain Fvs. Eukaryotic, e.g. mammalian, host cell expression systems may be used for production of larger antibody molecules, including complete antibody molecules. Suitable mammalian host cells include CHO, myeloma or hybridoma cells.

WO 01/94585 also provides a process for the production of an antibody molecule comprising culturing a host cell comprising a vector under conditions suitable for leading to expression of protein from DNA encoding the antibody molecule, and isolating the antibody molecule.

Preferably, the process for the production of the antibody molecule of WO 01/94585 comprises culturing *E. coli* comprising an *E. coli* expression vector comprising the DNA sequence under conditions suitable for leading to expression of protein from the DNA sequence and isolating the antibody molecule. The antibody molecule may be secreted from the cell or targeted to the periplasm by suitable signal sequences. Alternatively, the antibody molecule may accumulate within the cell's cytoplasm. Preferably the antibody molecule is targeted to the periplasm. Depending on the antibody molecule being produced and the process used, it is desirable to allow the antibody molecules to refold and adopt a functional conformation. Procedures for allowing antibody molecules to refold are well known to those skilled in the art.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

An embodiment of the present invention is a CP870 isomer having a PEG on Cys 214 of the light chain (CDP870-PEG-1214). The predominant CDP870 antibody form has a disulfide linkage between Cys 214 of the light chain and Cys 221 of the heavy chain and PEG attachment at Cys 227 of heavy chain. An unexpected positional PEG isomer was identified in the CDP870, which contains a PEG at Cys 214 of the light chain.

Another embodiment of the present invention is a CP870 isomer of having a PEG on Cys 214 of the light chain and a disulfide linkage between the Cys 221 of the heavy chain and Cys 227 of the heavy chain.

Another embodiment of the present invention is a CP870 isomer of having a PEG on Cys 214 of the light chain and an adduct at Cys 221 of the heavy chain and Cys 227 of the heavy chain. In a preferred embodiment the adducts are glutathione(s) or MEA.

Another embodiment is a composition comprises a CDP870 PEG positional isomer, having a PEG attached at Cys 214 of the light chain (CDP870-PEG-1214). In a preferred embodiment of the composition the CDP870-PEG-1214 isomer comprises between about 1% and 20% of the total antibody concentration. In a more preferred embodiment the CDP870-PEG-1214 isomer comprises between about 1% and 10% of the total antibody concentration. In a more preferred embodiment the CDP870-PEG-1214 isomer comprises between about 1% and 5% of the total antibody concentration. In a more preferred embodiment the CDP870-PEG-1214 isomer comprises less than about 5% of the total antibody concentration. The therapeutic or diagnostic composition or may be accompanied by other active ingredients including other antibody ingredients, for example anti-T cell, anti-IFNY or anti-LPS antibodies, or non-antibody ingredients such as xanthines.

In another embodiment the composition further comprises a CDP870 disulfide isomer, which contains a disulfide linkage between Cys 214 of the light chain and Cys 227 of the heavy chain (1214/h227). Preferably, the CDP870 disulfide isomer (1214/h227) has a PEG attached at Cys 221 of the heavy chain. Preferably, the CDP870-PEG-1214 positional isomer comprises about 1 to 20% of the total antibody concentration and the 1214/h227 disulfide isoform comprises about 20% to 50% of the total CDP870 antibody concentration. Preferably, the CDP870-PEG-1214 positional isomer comprises less than about 5% of the total antibody concentration and the h221/h227 disulfide isoform comprises about 30% to 40% of the total CDP870 antibody concentration.

The pharmaceutical compositions should preferably comprise a therapeutically effective amount of the antibody of the invention. The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective dose can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise effective amount for a human subject will depend upon the severity of the disease state, the general health of the subject, the age, weight and gender of the subject,' diet, time and frequency of administration, drug combination(s), reaction sensitivities and tolerance/response to therapy. This amount can be determined by routine experimentation and is within the judgement of the clinician. Generally, an effective dose will be from 0.0 1 mg/kg to 50 mg/kg, preferably 0.1 mg/kg to 20 mg/kg, more preferably about 15 mg/kg. As shown in the Examples below, doses of 1, 5 and 20 mg/kg have been used to treat patients suffering from rheumatoid arthritis.

Compositions may be administered individually to a patient or may be administered in combination with other agents, drugs or hormones.

The dose at which the antibody molecule of the present invention is administered depends on the nature of the condition to be treated, the degree to which the level of TNFα to be neutralised is, or is expected to be, raised above a desirable level, and on whether the antibody molecule is being used prophylactically or to treat an existing condition.

Thus, for example, where the product is for treatment or prophylaxis of a chronic inflammatory disease, such as rheumatoid arthritis, suitable doses of the antibody molecule of the present invention lie in the range of between 0.5 and 50 mg/kg, more preferably between 1 and 20 mg/kg and most preferably about 15 mg/kg. The frequency of dose will depend on the half-life of the antibody molecule and the duration of its effect.

If the antibody molecule has a short half-life (e.g. 2 to 10 hours) it may be necessary to give one or more doses per day. Alternatively, if the antibody molecule has a long half life (e.g. 2 to 15 days) it may only be necessary to give a dosage once per day, per week or even once every 1 or 2 months.

A pharmaceutical composition may also contain a pharmaceutically acceptable carrier for administration of the antibody. The carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient Preferred forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject The subjects to be treated can be animals. However, it is preferred that the compositions are adapted for administration to human subjects.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention.

Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be an antibody molecule. As such, it will be susceptible to degradation in the gastrointestinal tract Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

The present invention also provides the antibody molecule or compositions of the present invention for use in treating a disease mediated by TNFα.

The present invention further provides the use of the antibody molecule or composition according to the present invention in the manufacture of a medicament for the treatment of a disease mediated by TNFα.

The antibody molecule or composition of the present invention may be utilised in any therapy where it is desired to reduce the level of biologically active TNFα present in the human or animal body. The TNFα may be circulating in the body or present in an undesirably high level localised at a particular site in the body.

For example, elevated levels of TNFα are implicated in acute and chronic immune and immunoregulatory disorders, infections including septic, endotoxic and cardiovascular shock, inflammatory disorders, neurodegenerative diseases, malignant diseases and alcohol induced hepatitis. Details of the numerous disorders associated with elevated levels of TNFα, are set out in U.S. Pat. No. 5,919,452. The antibody molecule or composition of the present invention may be utilised in the therapy of diseases mediated by TNFα. Particularly relevant diseases which may be treated by the antibody molecule of the present invention include sepsis, congestive heart failure, septic or endotoxic shock, cachexia, adult respiratory distress syndrome, AIDS, allergies, psoriasis, TB, inflammatory bone disorders, blood coagulation disorders, burns, rejection episodes following organ or tissue transplant, Crohn's disease and autoimmune diseases, such as thyroiditis and rheumatoid- and osteo-arthritis.

Additionally, the antibody molecule or composition may be used: to reduce side effects associated with TNFα generation during neoplastic therapy; to eliminate or reduce shock-related symptoms associated with the treatment or prevention of graft rejection by use of an anti-lymphocyte antibody; or for treating multi-organ failure.

The antibody molecule or composition of the present invention is preferably used for treatment of rheumatoid- or osteo-arthritis.

The present invention also provides a method of treating human or animal subjects suffering from or at risk of a disorder mediated by TNFα the method comprising administering to the subject an effective amount of the antibody molecule or composition of the present invention.

The antibody molecule or composition of the present invention may also be used in diagnosis, for example in the in vivo diagnosis and imaging of disease states involving elevated levels of TNFα.

The present invention is further described by way of illustration only in the following examples, which refer to the accompanying Figures.

The complete content of all publications, patents, and patent applications cited in this disclosure are herein incorporated by reference as if each individual publication, patent, or patent application were specifically and individually indicated to incorporated by reference. Although the foregoing invention has been described in some detail by way of illustration and example for the purposes of clarity of understanding, it will be readily apparent to one skilled in the art in light of the teachings of this invention that changes and modifications can be made without departing from the spirit and scope of the present invention. The following examples are provided for exemplification purposes only and are not intended to limit the scope of the invention, which has been described in broad terms above.

EXAMPLES

Example 1

A CDP870 PEG positional isomer is produced in manufacturing where the branched PEG maleimide is conjugated to Cys 214 residue of the light chain, instead of the target Cys227 of the heavy chain. This material was identified by analysis of (1) peptide-PEG fragments separated by HPLC and analyzed by N-terminal sequencing and (2) the identification of non-pegylated heavy chain and pegylated light chain in extracts from reducing SDS-PAGE gel electrophoresis. Other techniques such as denaturing size exclusion HPLC have corroborated these findings. The reduction of samples to unpegylated heavy chain is evidence that the heavy/light chain association in the PEG positional isomer is due to noncovalent forces other than a disulfide bond.

What is claimed is:

1. An isolated antibody molecule which is a modified Fab fragment, the amino acid sequences of whose light chain (SEQ ID NO:1) and heavy chain (SEQ ID NO:2) are as depicted in FIG. 2, wherein a polyethylene glycol (PEG) moiety is attached at Cys 214 of the light chain.

2. The isolated antibody molecule of claim 1 further comprising a disulfide linkage between Cys 221 and Cys 227 of the heavy chain.

3. A therapeutic or diagnostic composition comprising the isolated antibody molecule of claim 1 in association with a pharmaceutically acceptable carrier.

4. A therapeutic or diagnostic composition comprising the isolated antibody molecule of claim 2 in association with a pharmaceutically acceptable carrier.

* * * * *

UNITED STATES PATENT AND TRADEMARK OFFICE
CERTIFICATE OF CORRECTION

PATENT NO.      : 7,601,817 B2
APPLICATION NO. : 10/515677
DATED           : October 13, 2009
INVENTOR(S)     : Ned M. Mozier It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 908 days.

Signed and Sealed this

Fifth Day of October, 2010

David J. Kappos
*Director of the United States Patent and Trademark Office*

SEQUENCE LISTING

<160> NUMBER OF SEQ ID NOS: 2

<210> SEQ ID NO 1
<211> LENGTH: 214
<212> TYPE: PRT
<213> ORGANISM: artificial
<220> FEATURE:
<223> OTHER INFORMATION: humanized TNF alpha antibody light chain

<400> SEQUENCE: 1

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Phe Leu Tyr Ser Gly Val Pro Tyr Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
```

-continued

```
                195                 200                 205
Phe Asn Arg Gly Glu Cys
    210

<210> SEQ ID NO 2
<211> LENGTH: 224
<212> TYPE: PRT
<213> ORGANISM: artificial
<220> FEATURE:
<223> OTHER INFORMATION: humanized TNF alpha heavy chain antibody

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met Asn Trp Val Arg Gly Leu Glu Trp Met Gly Trp Ile Asn Thr
        35                  40                  45

Tyr Ile Gly Glu Pro Ile Tyr Ala Asp Ser Val Lys Gly Arg Phe Thr
    50                  55                  60

Phe Ser Leu Asp Thr Ser Lys Ser Thr Ala Tyr Leu Gln Met Asn Ser
65                  70                  75                  80

Leu Arg Ala Glu Asp Thr Ala Val Tyr Tyr Cys Ala Arg Gly Tyr Arg
                85                  90                  95

Ser Tyr Ala Met Asp Tyr Trp Gly Gln Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Ala Ala
    210                 215                 220
```